US008361928B2

(12) United States Patent
Baley et al.

(10) Patent No.: US 8,361,928 B2
(45) Date of Patent: Jan. 29, 2013

(54) SUPPRESSION OF FOLIAR AND SOILBORNE PATHOGENS

(75) Inventors: George J. Baley, Webster Groves, MO (US); Kimberlee K. Kidwell, Pullman, WA (US); Timothy C. Paulitz, Pullman, WA (US)

(73) Assignees: Washington State University Research Foundation, Pullman, WA (US); The United States of America as Represented by the Secretary of Argiculture, Washington, DC (US)

( * ) Notice: Subject to any disclaimer, the term of this patent is extended or adjusted under 35 U.S.C. 154(b) by 1890 days.

(21) Appl. No.: 10/567,367

(22) PCT Filed: Oct. 27, 2004

(86) PCT No.: PCT/US2004/035807
§ 371 (c)(1),
(2), (4) Date: Feb. 7, 2006

(87) PCT Pub. No.: WO2005/041669
PCT Pub. Date: May 12, 2005

(65) Prior Publication Data
US 2006/0223707 A1 Oct. 5, 2006

Related U.S. Application Data

(60) Provisional application No. 60/515,339, filed on Oct. 28, 2003, provisional application No. 60/532,758, filed on Dec. 24, 2003.

(51) Int. Cl.
*A01N 57/20* (2006.01)
*A01P 3/00* (2006.01)
(52) U.S. Cl. .................................... 504/206; 514/114

(58) Field of Classification Search ............ 504/206; 514/114
See application file for complete search history.

(56) References Cited

U.S. PATENT DOCUMENTS

| 4,609,668 | A  | * | 9/1986 | Schaub et al. | 514/383 |
| 7,268,274 | B2 | * | 9/2007 | Chen et al. | 800/300 |
| 7,608,761 | B2 | * | 10/2009 | Baley et al. | 800/300 |
| 2003/0077801 | A1 | * | 4/2003 | Andrews et al. | 435/196 |
| 2005/0223425 | A1 | * | 10/2005 | Clinton et al. | 800/279 |

OTHER PUBLICATIONS

Sanogo et al., Effects of herbicides on *Fusarium solani* f. sp. Glycines and Development of Sudden Death Syndrome in Glyphosate-Tolerant Soybean, Phytopathology, vol. 90 No. 1, pp. 57-64, 2000.*
Zhou et al., Field Efficacy Assessment of Transgenic Roundup Ready Wheat, Crop Science, vol. 43, 3; p. 1072-1075, May/Jun. 2003.*
Harikrishnan et al., Effects on Root Rot and Damping-off caused by *Rhizoctonia solani* in Glyphosate-Tolerant Soybean, Plant Disease, vol. 86 No. 12, pp. 1369-1373, 2002 et al.*
CABA abstract 1994:82029 (1994).*

* cited by examiner

*Primary Examiner* — John Pak
(74) *Attorney, Agent, or Firm* — Whitham Curtis Christofferson & Cook, PC

(57) ABSTRACT

Disclosed herein is a method for increasing the production of crops, particularly wheat and soybean, using herbicide resistant cultivars. In one aspect of this method, the method increases crop yield by diminishing the impact of the root diseases caused by *Gaeumannomyces* and *Rhizoctonia* species by treating the crop with an herbicide, in particular glyphosate. In another aspect the method for treating crops reduces the effects foliar pathogens and diseases, particularly fungal pathogens, such as rusts, including soybean rust, stem rust, stripe rust and leaf rust.

18 Claims, 3 Drawing Sheets

SUPPRESSION OF FOLIAR AND SOILBORNE PATHOGENS

CROSS REFERENCE TO RELATED APPLICATION

Figure 1:
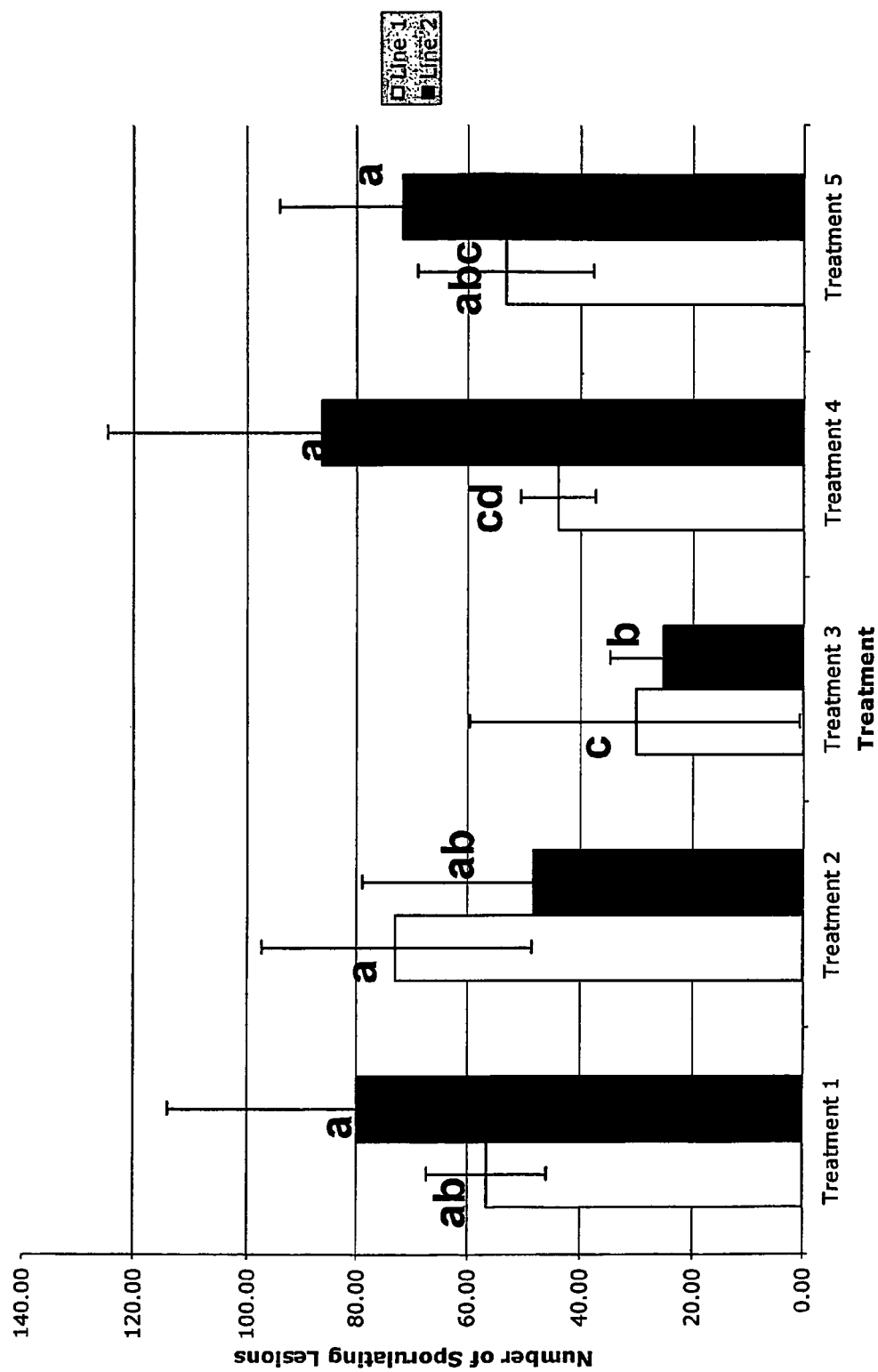
Figure 2:
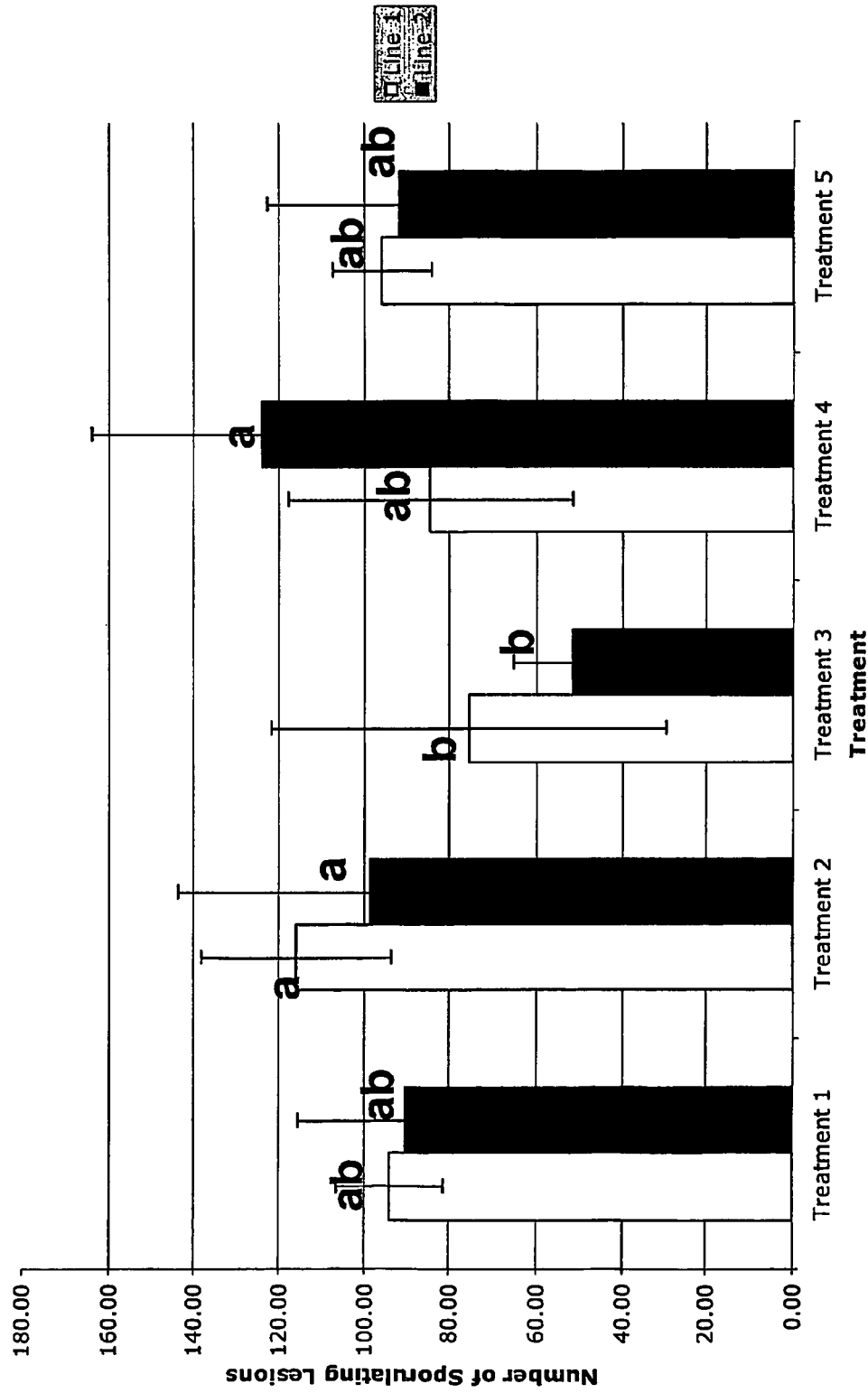
Figure 3:
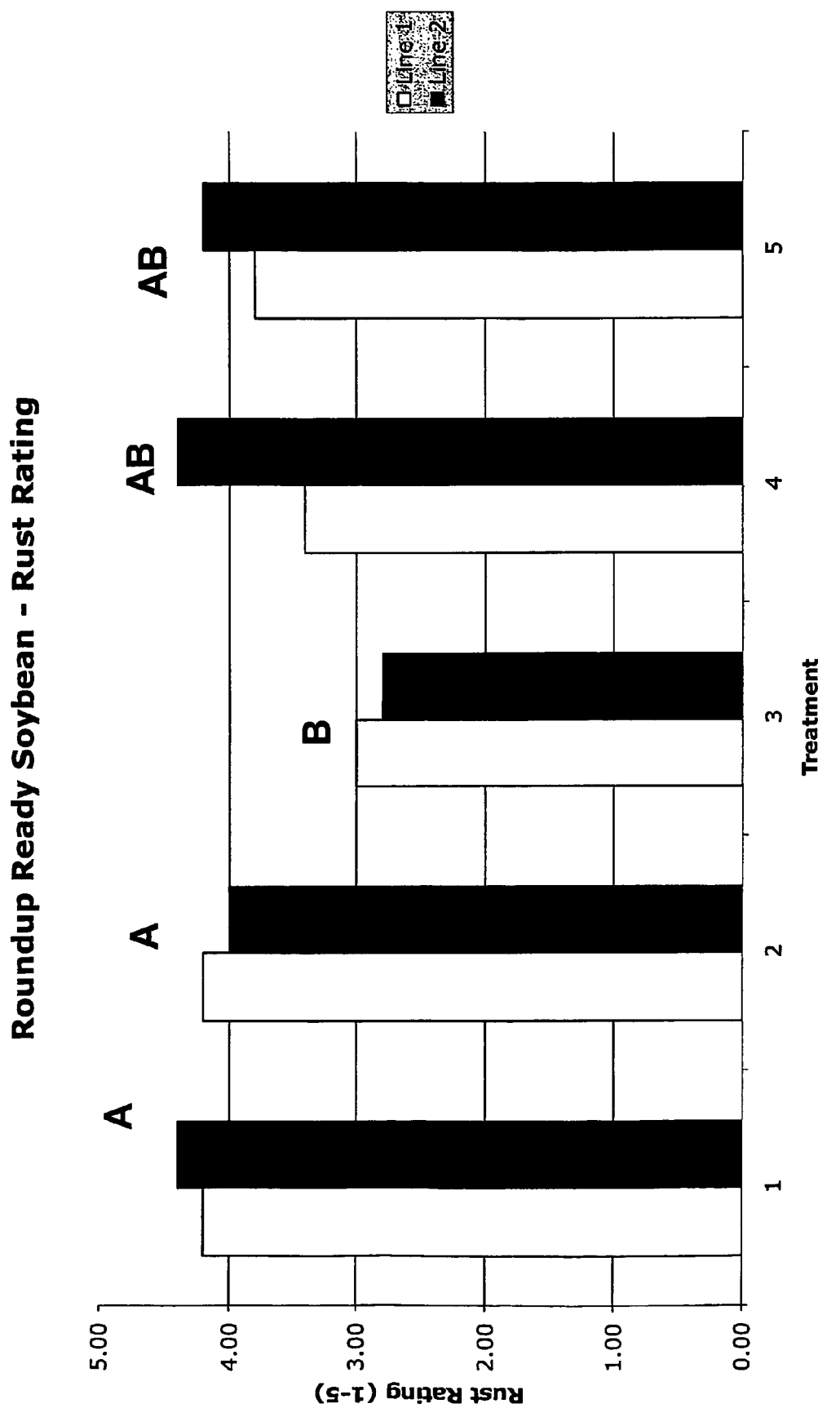

This application claims the benefit of U.S. Provisional Patent Application No. 60/515,339 filed Oct. 28, 2003, and U.S. Provisional Patent Application No. 60/532,758 filed Dec. 24, 2003, both of which are incorporated herein by reference.

ACKNOWLEDGEMENT OF GOVERNMENT SUPPORT

The Federal government may have certain rights in this technology pursuant to USDA Biotechnology Risk Assessment Research Grant number 2001-03734.

FIELD

This disclosure concerns methods for increasing the yield of crops that subject to disease pressure, particularly from seed borne, soil borne or foliar pathogens, such as fungi.

BACKGROUND

Commercial farming is a critical part of the economy. However crops are subject to near constant attack by insects, fungi, bacteria and other pathogens. When such pathogens encounter susceptible crops, such attacks can result in lower yield quality and can even destroy entire crops. Thus, pathogens cause substantial economic harm to growers and in some areas of the world contribute to famine.

Traditionally, farmers have relied upon conventional tillage methods to disrupt the soil and thereby control weeds, pathogens and volunteer crops. However, the current trend, particularly in the Pacific Northwest region, is to use no-till or direct seed crop production methods to reduce soil erosion and the accompanying environmental degradation associated with conventionally tilled fields. No-till and direct seeding methods aim to reduce environmental degradation but generally require the use of herbicides to control weeds and volunteer crops.

Typically growers apply herbicides prior to planting to control weeds since the crop itself may be susceptible to the herbicide. However the development of herbicide resistant wheat varieties raises the possibility of increasing wheat yields by applying the herbicide to the standing crop. Unfortunately, weeds dying in the standing crop have been demonstrated to result in carryover of fungal pathogens, which typically are unaffected by herbicides, from the dying weeds to the standing wheat crop. Indeed, U.S. Pat. No. 5,972,689 to Cook et al. (Cook) discloses that spraying with an herbicide such as glyphosate controls weeds, but favors the development of *Rhizoctonia* root rot in wheat. Because wheat is particularly susceptible to fungal pathogens, this carryover or "green-bridge" is a serious problem.

This green-bridge effect often leads to yield reductions associated with increased disease pressure which are the result of increased soilborne pathogens present on dying herbicide-sensitive volunteer and/or weeds. For example, *R. solani* significantly reduced grain yields of glyphosate-sensitive barley when glyphosate was applied three days before planting. However, no significant yield depression was detected when glyphosate was applied in the fall or three weeks prior to planting (Smiley et al. *Plant Dis.* 1992, 76, 937-942). These results demonstrate that a fresh source of *R. solani* inoculum, from the dying volunteer and weeds treated with glyphosate three days prior to planting, acted as a green-bridge for the fungus to infect barley planted shortly after herbicide application.

Another fungal disease of concern, take-all, is caused by *Gaeumannomyces graminis* var. *tritici* (Ggt), which has been a persistent pathogen plaguing wheat around the world for over a hundred years. Take-all (Ggt) disease is present in the roots, crown, and basal stem of infected wheat plants. Severe Ggt infection can decrease grain yields by as much as 50%. Symptoms of infection include stunting, blackened lower stems, and white heads. Take-all will commonly put out "runner-hyphae" to neighboring plants, so that a single site of infection is sufficient to cause multiple infections. Persistence through a green-bridge effect can occur similar to that reported for *R. solani*. Studies conducted in New Zealand have shown that treatment of cereals with glyphosate increases the levels of infection with Ggt due to the green-bridge effect of the herbicide on couch grass (Harvey et al. *Aglink* 1/3000/3/82, 1982, Ministries of Agriculture and Fisheries, Wellington, New Zealand). The most successful current form of Ggt control is through crop rotation, which is not always satisfactory for wheat production.

Nineteen *Pythium* species have been reported to be pathogenic to wheat roots. *Pythium* inoculum will remain active within the upper soil layer for years, utilizing residues as a source of nutrients. *Pythium* is considered to be a primary colonizer and infection levels can be reduced by removing straw and debris from the field. Unfortunately, this is not an option in a no-till system.

The interaction between glyphosate treated plants and infection by *Pythium* spp. has been investigated with numerous crop species. Soilborne *Pythium* spp. were found to be the first and predominant root colonizers of glyphosate treated plants (Levesque et al. *Mycological Research* 1993, 20, 307-312). This is an important observation since *Pythium* damage is often overlooked by growers, even though significant yield loss resulting from *Pythium* infection can occur.

Another group of important pathogens that affect wheat include foliar fungal pathogens, such rusts. Rust pathogens are parasitic fungi that infect wheat, barley, oats, beans, corn, sorghum, and other plants. Each rust pathogen is generally specific to its host and the location on the plant where infection occurs. The stem rust pathogen (*Puccinia graminis f.* sp. *tritici*) is a fungus that principally infects the leaf sheath of wheat plants. The leaf rust pathogen (*Puccinia recondita f.* sp. *tritici*) infects wheat plants through the stomates. The stripe rust pathogen (*Puccinia striiformis*) is similar to leaf rust, but differs in that infections appear systemic due to colonization patterns on wheat leaves.

Soybean rust is another serious rust pathogen that causes crop losses. It has not yet been detected in the continental United States, but the fact that it is principally spread by wind-borne spores indicates it may eventually reach major soybean growing areas in the United States. Soybean rust is caused by two fungal species, *Phakopsora pachyrhizi* and *Phakopsora meibomiae*. It has been reported in various countries including Australia, China, Korea, India, Japan, Nepal, Taiwan, Thailand, the Philippines, Mozambique, Nigeria, Rwanda, Uganda, Zimbabwe, South Africa, Brazil, Argentina, and Paraguay. *P. meibomiae* has been reported to be a weak pathogen. However, *Phakopsora pachyrhizi* is much more aggressive and recent introductions of *P. pachyrhizi* have rapidly spread causing severe damage in Zimbabwe, South Africa, Paraguay, and Brazil. Yield losses have been reported from 10-80%. Other important fungal pathogens that affect soybeans include root rot caused by various species of *Phytophthora*.

There are few methods for controlling fungal diseases in wheat and soybeans, and none of these methods are widely accepted as being commercially viable. For example, some root rot diseases can be controlled through of crop rotation, that is, by not growing wheat in the same field more than every third or fourth year. However, like most other enterprises, agriculture has forced farmers to specialize in order to compete. The United States grows some 150 different crops, but fewer than 15 of these crops (including wheat and barley) occupy more than 90% of U.S. cropland, with the vast majority of farms specialized in the production of a single crop year after year on the same land, or two or at most three crops grown in a rotation on any given farm. Many wheat farms in areas well-suited to cereals tend to grow wheat every year or at least every other year in the same fields. Moreover, in certain regions, such as in the Pacific Northwest, leguminous crops commonly used in rotations do not bring the same levels of financial returns as do continuous wheat cropping systems (see, Cook and Veseth *Wheat Health Management*; American Phytopathological Society: St. Paul, Minn., 1991). Therefore, crop rotation is not a feasible economic solution to reduce disease pressure in a continuously cropped no-till production system.

Many diseases of wheat, barley, and other crops are controlled by breeding varieties of the crops with resistance to the pathogens. However, this approach has not worked for certain fungal diseases of wheat, particularly root diseases. No commercial wheat is available that has resistance to take-all, *Rhizoctonia* root rot, or *Pythium* root rot. Moreover, rust pathogens mutate at a relatively high rate, and therefore new rust-resistant cultivars of wheat are needed approximately every seven years.

Another method that is currently used to combat fungal infections is the topical application of fungicides. Fungicides, although effective, are prohibitively expensive for growers and typically must be applied as a preventative, even if it is not certain that the plants will be infected. Moreover many of the fungicides previously used have been withdrawn by the EPA. Compounds that are currently used are more easily degraded and therefore are less harmful to the environment, but fungi can quickly develop resistance to these compounds. Thus, fungicide applications are even less desirable than before.

SUMMARY OF THE DISCLOSURE

Disclosed herein is a method for conferring resistance to pathogens on crops, including wheat and soybeans. In one embodiment, the method includes treating a standing crop with an herbicide. In one aspect, the method includes treating a crop with an herbicide, which increases the crop's resistance to fungal pathogens. In one aspect of this method, the method increases crop yield by diminishing the impact of the root diseases caused by *Gaeumannomyces* and *Rhizoctonia* species. In another aspect, the method increases the crop's resistance to foliar pathogens, particularly fungal pathogens such as rusts caused by various species, including stem rust, stripe rust, leaf rust and soybean rust.

Typically, the disclosed methods result in increased crop yields. Any increase in crop yield is desirable, however typically the method produces from about 5% to about 25% greater yield, and more typically from about 5% to about 15% greater yield relative to an untreated crop.

The herbicide used in embodiments of the disclosed methods typically includes at least one of a sulfamoylurea, sulfonylcarboxamide, sulfonamide, sulfonylurea or glyphosate. In one aspect a combination of herbicides, such as two or more of the herbicides listed above or one of the listed herbicides and one or more herbicide not listed, can be applied to the crop. Typically the herbicide or herbicides are selected with reference to the particular wheat cultivar to be treated, for example, an herbicide to which the particular cultivar is resistant can be selected.

In one embodiment, the resistance of crops to various pathogens is induced by applying an effective amount of an agricultural grade formulation of a glyphosate-based herbicide (such as ROUNDUP® brand herbicide produced by Monsanto, St. Louis, Mo.) to a glyphosate resistant crop after emergence. Typically, the effective amount of active ingredient applied is from about 0.5 kg/ha to about 3.0 kg/ha, and more typically from about 1.0 kg/ha to about 1.5 kg/ha. In one embodiment wheat is treated with formulations containing glyphosate at a density from about 0.5 kg/ha to about 1.5 kg/ha of glyphosate. In another embodiment a soybean crop is treated with from about greater than about 1.0 kg/ha, such as from about 1.5 to about 3.0 kg/ha of glyphosate. In one aspect of the method, an amount of glyphosate less than that typically recommended for weed control is effective to confer or induce pathogen resistance to a crop.

In one embodiment a crop is treated with glyphosate at a growth stage not currently recommended for glyphosate treatment. For example, in one embodiment glyphosate is applied to wheat at or after the 3 leaf stage, such as between the 3 leaf stage and the flowering stage. In another embodiment glyphosate is applied to soybean at growth stage after emergence and before the flowering stage. In one aspect, glyphosate is applied after symptoms of pathogen infection appear.

In embodiments of the method, treatment of herbicide resistant crop with an herbicide reduces disease on the crop for an extended period of time, and particularly for longer than the herbicide is active as an herbicide after the treatment. Typically, the disease reduction extends for at least about seven days after the treatment; more typically extends for at least about 21 days, and in certain examples extends for the life of the crop.

In another embodiment of the method, a crop is treated with an herbicide prior to emergence, and treated with the same or a different herbicide after emergence. In yet another embodiment of the method a crop is treated with two or more separate applications of one or more herbicide.

BRIEF DESCRIPTION OF THE DRAWINGS

FIG. 1 is a bar graph recording the number of sporulating lesions present 14 days following inoculation of two different soybean cultivars with soybean rust spores and subject to five different conditions, demonstrating the suppression of soybean rust accompanying glyphosate treatment of soybeans before and after inoculation with rust (treatments followed by the same letters are not significantly different at P=0.05, LSD test).

FIG. 2 is a bar graph recording the number of sporulating lesions present 21 days following inoculation of two different soybean cultivars with soybean rust spores and subject to five different conditions, demonstrating the suppression of soybean rust accompanying glyphosate treatment of soybeans before and after inoculation with rust (treatments followed by the same letters are not significantly different at P=0.05, LSD test).

FIG. 3 is a bar graph recording observed rust rating following inoculation of the soybeans with rust and subject to five different treatment conditions (treatments followed by the same letter are not significantly different at P=0.05, Kruskal-Wallis One-Way Nonparametric test).

DETAILED DESCRIPTION

I. Introduction

The present disclosure illustrates the surprising result that the treatment of herbicide resistant wheat, particularly glyphosate resistant wheat, with an herbicide, such as glyphosate, reduces disease caused by pathogens in the wheat. Moreover, the wheat exhibits persistently superior pathogen resistance over an extended period of time, after the herbicide is no longer effective as an herbicide. In one embodiment, the deterrence of the pathogen is due to the accumulation of glyphosate in the tissues the plant. In one embodiment the herbicide acts indirectly by inducing systemic disease resistance.

II. Herbicides and Herbicide Resistant Crops

Disease reduction on herbicide resistant crops can be accomplished according to the methods disclosed herein. Suitable herbicides and herbicide resistant crops are known and will be readily apparent to those of ordinary skill in the art. Moreover, methods for producing transgenic herbicide resistant crops, including, without limitation, wheat and soybeans, are disclosed by U.S. Pat. Nos. 6,635,806, 6,803,501, 6,750,383, which are incorporated herein by reference.

One herbicide for which resistant crops, including resistant wheat and soybean cultivars, have been developed is N-phosphonomethylglycine, commonly referred to as glyphosate. Glyphosate is the active ingredient in glyphosate herbicides, such as ROUNDUP® brand herbicide produced by Monsanto (St. Louis, Mo.). Typically, glyphosate is formulated as a water-soluble salt such as an ammonium, alkylamine, alkali metal or trimethylsulfonium salt. One of the most common formulations is the isopropylamine salt of glyphosate, which is the form employed in ROUNDUP® brand herbicide.

Glyphosate is conventionally applied as an aqueous solution to the foliage of plants to be killed, where it is taken up into the leaves and transported throughout the plant. Commercial formulations of glyphosate may also include one or more surfactants to facilitate penetration of the active ingredient into the plant leaves, as well as compounds to enhance rainfastness. Numerous U.S. patents disclose various formulations of glyphosate and methods for their use, including U.S. Pat. Nos. 4,405,531; 5,118,338; 5,196,044; 5,639,711; 5,652,197; 5,679,621; 5,750,468; 6,207,617; and 6,455,473. Each of these patents is incorporated herein by reference.

Glyphosate inhibits the shikimic acid pathway, which is responsible for the biosynthesis of aromatic compounds including amino acids, such as tryptophan, phenylalanine and tyrosine, as well as several secondary metabolites. Specifically, glyphosate inhibits the conversion of phosphoenolpyruvic acid (PEP) and 3-phosphoshikimic acid to 5-enolpyruvyl-3-phosphoshikimic acid by inhibiting the enzyme 5-enolpyruvylshildmate-3-phosphate synthase (hereinafter referred to as EPSP synthase or EPSPS). For purposes of the present disclosure, the term "glyphosate" is intended to include any herbicidally effective form of N-phosphonomethylglycine (including any salt thereof) and other forms which result in the production of the glyphosate anion in plants.

Glyphosate resistant crops, including glyphosate resistant wheat and soybeans, are well known to those of ordinary skill in the art. Examples of glyphosate resistant wheat are disclosed in U.S. Pat. Nos. 5,463,175; 5,463,175; and 6,153,812. Production of lines of other plant species, including soybean, expressing a glyphosate-tolerance gene may be produced by techniques known in the art. See, e.g. U.S. Pat. Nos. 5,312,910; 5,310,667; 5,463,175. Each of these patents is incorporated herein by reference.

III. Methods and Examples

Because herbicide treatment, including glyphosate treatment, typically impairs certain plant defense mechanisms, dying herbicide sensitive plants can function as a green-bridge, transferring pathogens to a standing crop. For example, glyphosate blocks the production of phenolic compounds, such as lignin precursors and phytoalexins that are components of the defense mechanisms and confer disease resistance. Because glyphosate causes the breakdown of plant defenses, glyphosate renders glyphosate sensitive plants susceptible to pathogen invasion. This supplemental effect of glyphosate treatment has been termed Glyphosate Synergistic Interaction (GSI). GSI also provides a source or inoculum of pathogens that can attack the glyphosate resistant crop, thereby worsening the green-bridge effect.

As demonstrated herein, it has been surprisingly found that herbicides can function indirectly to reduce pathogen damage to wheat. This result is particularly surprising because herbicides have previously been shown to exacerbate the problems caused by fungal pathogens. Moreover, the herbicides have little or no direct anti-fungal activity and indeed the pathogen resistance is shown to be effective well after the herbicide itself dissipates from the treatment site. Accordingly, disclosed herein are methods for increasing disease resistance in wheat, examples of which include providing an herbicide resistant wheat crop and treating the crop with an herbicide, thereby conferring disease resistance on the crop for an extended period of time.

One of the herbicides effective in the present methods, glyphosate, is currently applied to glyphosate sensitive wheat fields (prior to emergence of the crop) by producers in the fall or spring as an inexpensive yet effective way of controlling weed competition. Glyphosate has a wide spectrum of activity and controls 97% of the world's worst weed problems. However, glyphosate has not been shown to be effective against fungal pathogens, (see, Franz, J. E. Discovery Development and Chemistry of Glyphosate. In, *The Herbicide Glyphosate*, Butterworths, London, 1985, pp 3-17). Moreover, some previous studies have suggested that glyphosate encourages the growth of toxic fungi.

Disclosed embodiments of the present methods using glyphosate resistant wheat and soybean crops provide this same level of weed control during the early crop growth stages, and moreover reduce the effect of pathogenic organisms and particularly fungal pathogens on wheat and soybean crops. Moreover, embodiments of the present methods are effective for treating crops that are already infected with a pathogen, having a curative effect on such crops. Therefore, in addition to eliminating weed competition, the present methods reduce losses to plant diseases, thereby decreasing herbicide costs, increasing grain yields, and enhancing profitability.

For example, under severe stripe rust conditions, two Bobwhite cultivars that had not been treated with RoundUp were heavily infested with stripe rust, whereas glyphosate treated glyphosate resistant Bobwhite exhibited only moderate stripe rust symptoms. Bobwhite cultivars sprayed with Buctril/Harmony Extra (Buctril is commercially available from Bayer CropScience, and Harmony Extra is commercially available from DuPont) or the untreated control displayed severe stripe rust susceptibility symptoms and matured 2-3 weeks earlier than NILs treated with RoundUp. Buctril/Harmony Extra treated glyphosate resistant Bobwhite produced significantly (P=0.01) less grain than the glyphosate resistant Bobwhite treated with glyphosate, regardless of root disease treatment. Visual differences in stripe rust severity typically were not apparent until 21 days after herbicide application, which notably is well beyond the time after application that the herbicide exerts its direct herbicidal effects.

The present results in both wheat and soybean are surprising for several reasons, including that glyphosate was not previously found to be effective for suppressing disease in glyphosate resistant crops. The results presented herein also are surprising because glyphosate is directly effective as an herbicide for only a short time and is not persistent in herbicidally effective amounts. These results demonstrate that glyphosate application suppresses pathogen growth for an extended period of time. The method is particularly effective in hindering the colonization of leaf tissue by foliar pathogens. Moreover, the pathogen suppression extends to root pathogens, such as *Rhizoctonia* and Ggt.

In one embodiment, the methods disclosed herein can be used to treat a crop, such as wheat or soy crops, that are infected with a pathogen, such as a fungal pathogen, including seed borne, soil borne or foliar fungal diseases. For example, the treatment of infected crops with glyphosate is demonstrated herein to decrease fungal colonization of crops and to increase crop yield. This result is surprising because the fungal pathogens, such as stripe rust, soybean rust and the like, previously have not been thought to be susceptible to glyphosate. In one embodiment the treatment of the crops includes two or more separate applications of glyphosate. Thus, according to the embodiments disclosed herein crop yields can be increased by treating a crop before symptoms of infection are evident, following the appearance of infection, or both. In exemplary embodiments, treatment of wheat and soybean both before and after the emergence of foliar fungal infection resulted in increased crop yield; In one embodiment, the crops are treated with from about 0.5 kg/ha to about 3.0 kg/ha of glyphosate in one or more applications. In one embodiment, from about 0.5 kg/ha to about 1.5 kg/ha, such as from about 1.0 kg/ha to about 1.5 kg/ha of glyphosate is applied. In one embodiment a first application of glyphosate of from about 0.5 kg/ha to about 2.0 kg/ha is made, followed by at least a second application of from about 0.5 kg/ha to about 2.0 kg/ha. In one aspect of this embodiment the crop is wheat and at least one application is made between the 3 leaf stage and the flowering stage. In another aspect of the method the crop is soybean and at least one application is made between emergence and the flowering stage.

As demonstrated in the examples below, the reduced disease susceptibility of wheat treated according to the method also was responsible for increased grain yields observed for glyphosate treated glyphosate resistant cultivars across trial growing locations, regardless of disease treatment.

The foregoing disclosure is further explained by the following non-limiting examples.

Example 1

This example describes the response of glyphosate resistant and glyphosate sensitive spring wheat to inoculation with soil pathogens as judged by wheat yield. Inoculation simulates the green-bridge effect of dying weeds and volunteer in a standing wheat crop. The soil pathogens assessed were: *Rhizoctonia solani* isolate AG-8 and *Gaeumannomyces graminis* var. *tritici*. These pathogenic strains are prevalent in the Pacific Northwest and were isolated from the region. They have been maintained by the Department of Plant Pathology and USDA researchers at Washington State University.

Near isogenic lines (glyphosate resistant and glyphosate sensitive) of Westbred 926 and Bobwhite were seeded using a no-till drill at three different sites (Lind, Davenport and Pullman, Wash.).

To introduce the root pathogens into the wheat seed for distribution into the field, oat seeds, autoclaved and sterilized, were inoculated for each soilborne pathogen using isolated pathogen cultures. Oat seeds that were non-inoculated, but sterilized and autoclaved, served as a control. Following two weeks of pathogen growth, the inoculated oat seeds were dried down for 2 days and screened for potential contamination. To establish a green-bridge, a mixture of 15% barley and 20% oat inoculum seeds (by weight) were planted using a small plot no-till drill. One week after planting the introduced green-bridge, the wheat isolines were planted in rows adjacent to the barley green-bridge rows in a randomized, split-plot design, replicated in five randomized blocks. Inoculum treatment served as the main plot, and response to herbicides as the subplot factor.

The results for Ggt and *Rhizoctonia* inoculation compared to non-inoculated controls are illustrated in Table 1. In summary, with reference to Table 1, inoculation of wheat as described above can result in depressed yields, as demonstrated in Lind in 2002. Yield losses are often more severe in areas of lower rainfall such as Lind.

TABLE 1

Wheat yield depression due to fungal inoculation, without herbicide treatments, 2002.

| Inoculation | Herbicide | Location | Yield (bu/acre) |
|---|---|---|---|
| None | None | Lind | 13.5 |
| Ggt | None | Lind | 12.0 |
| *Rhizoctonia* | None | Lind | 12.9 |
| None | None | Davenport | 21.5 |
| Ggt | None | Davenport | 24.6 |
| *Rhizoctonia* | None | Davenport | 23.3 |
| None | None | Pullman | 46.5 |
| Ggt | None | Pullman | 47.0 |
| *Rhizoctonia* | None | Pullman | 47.5 |

Example 2

This example describes the effect of herbicide treatment on spring wheat, averaged over all disease treatments, planted as described in Example 1. The appropriate herbicide was applied to each trial once the plants reached the 4-5 leaf stage with a custom built hand-pulled sprayer outfitted with a boom with a length of 16 feet with spray shields on the side to minimize drift. In this manner, an entire plot was treated at once with the appropriate herbicide rate. Entries that were resistant to glyphosate were treated with ROUNDUP® brand herbicide (0.63 kg/ha), available from Monsanto, St. Louis, Mo. Herbicide sensitive and resistant entries were treated with a common broadleaf herbicide treatment (Buctril/Harmony) or a no-spray control. Introduced green-bridge barley and any other weeds were manually removed 7-10 days after spray treatment to simulate the time required for ROUNDUP to take effect and maintained weed-free conditions to provide an accurate comparison to commercial weed management strategies needed to assess potential herbicide/disease interactions.

The results of the herbicide treatment are recorded in Table 2. With reference to Table 2, treatment of glyphosate resistant wheat with glyphosate resulted in higher yields in each trial.

TABLE 2

Effect of herbicide treatment on glyphosate resistant wheat averaged over all fungal inoculation treatments, demonstrating increased yield associated with glyphosate treatment.

| Herbicide Resistance | Herbicide | Location | Yield (bu/acre) |
|---|---|---|---|
| None | None | Lind | 12.8 |
| None | Buctril/Harmony | Lind | 12.7 |
| glyphosate res. | Glyphosate | Lind | 14.2 |
| None | None | Davenport | 23.2 |
| None | Buctril/Harmony | Davenport | 24.2 |
| glyphosate res. | Glyphosate | Davenport | 28.9 |
| None | None | Pullman | 47.0 |
| None | Buctril/Harmony | Pullman | 45.6 |
| glyphosate res. | Glyphosate | Pullman | 56.5 |

Example 3

This example describes the assessment of the disease response of non-inoculated glyphosate resistant spring wheat as described in Example 1 and treated with glyphosate in comparison to inoculated near isogenic lines of glyphosate sensitive spring wheat. The results, recorded in Table 3, demonstrate increased yield accompanying glyphosate treatment of non-inoculated wheat.

TABLE 3

Yields of non-inoculated wheat demonstrating increased yield of glyphosate resistant wheat due to glyphosate treatment, 2002.

| Inoculation | Herbicide Resistance | Herbicide | Location | Yield (bu/acre) |
|---|---|---|---|---|
| none | None | None | Lind | 13.5 |
| none | None | Buctril/Harmony | Lind | 12.8 |
| none | glyphosate res. | glyphosate | Lind | 14.2 |
| none | None | None | Davenport | 24.6 |
| none | None | Buctril/Harmony | Davenport | 23.6 |
| none | glyphosate res. | glyphosate | Davenport | 29.1 |
| none | None | None | Pullman | 47.0 |
| none | None | Buctril/Harmony | Pullman | 45.0 |
| none | glyphosate res. | glyphosate | Pullman | 55.6 |

Thus treatment of glyphosate-resistant wheat lines with glyphosate increases yield, even in the absence of additional pathogen inoculum.

Example 4

This example describes the assessment of the disease response of glyphosate resistant spring wheat inoculated with Ggt as described in Example 1 and treated with glyphosate in comparison to inoculated near isogenic lines of glyphosate sensitive spring wheat.

The effect of herbicide treatment on the yield of glyphosate resistant wheat inoculated with Ggt is illustrated in Table 4. The yield for glyphosate treated, glyphosate resistant, Ggt inoculated wheat was significantly superior ($P \leqq 0.05$) as compared to both untreated and Buctril/Harmony treated glyphosate sensitive wheat at each location.

TABLE 4

Yields of Ggt inoculated wheat demonstrating increased yield of glyphosate resistant wheat due to glyphosate treatment.

| Inoculation | Herbicide Resistance | Herbicide | Location | Yield (bu/acre) |
|---|---|---|---|---|
| Ggt | None | None | Lind | 12.0 |
| Ggt | None | Buctril/Harmony | Lind | 13.6 |
| Ggt | glyphosate res. | glyphosate | Lind | 14.4 |
| Ggt | None | None | Davenport | 21.5 |
| Ggt | None | Buctril/Harmony | Davenport | 24.2 |
| Ggt | glyphosate res. | glyphosate | Davenport | 28.7 |
| Ggt | None | None | Pullman | 46.5 |
| Ggt | None | Buctril/Harmony | Pullman | 41.0 |
| Ggt | glyphosate res. | glyphosate | Pullman | 57.0 |

Example 5

This example describes the assessment of the disease response of glyphosate resistant spring wheat inoculated with *Rhizoctonia solani* as described in Example 1 and treated with glyphosate in comparison to inoculated near isogenic lines of glyphosate sensitive spring wheat.

With reference to Table 5, glyphosate treatment of glyphosate resistant wheat resulted in enhanced yield at each location relative to untreated and conventionally (Buctril/Harmony) treated glyphosate sensitive wheat.

TABLE 5

Yields of *Rhizoctonia* inoculated wheat demonstrating increased yield of glyphosate resistant wheat due to glyphosate treatment.

| Inoculation | Herbicide Resistance | Herbicide | Location | Yield (bu/acre) |
|---|---|---|---|---|
| *Rhizoctonia* | None | None | Lind | 12.9 |
| *Rhizoctonia* | None | Buctril/Harmony | Lind | 11.7 |
| *Rhizoctonia* | glyphosate res. | glyphosate | Lind | 14.0 |
| *Rhizoctonia* | None | None | Davenport | 23.3 |
| *Rhizoctonia* | None | Buctril/Harmony | Davenport | 24.7 |
| *Rhizoctonia* | glyphosate res. | glyphosate | Davenport | 29.0 |
| *Rhizoctonia* | None | None | Pullman | 47.5 |
| *Rhizoctonia* | None | Buctril/Harmony | Pullman | 50.6 |
| *Rhizoctonia* | glyphosate res. | glyphosate | Pullman | 53.9 |

*Rhizoctonia* and Ggt naturally prevail in areas receiving low and high levels of precipitation, respectively. In trials planted in the low and high rainfall zones, grain yields of NILs treated with Buctril/Harmony Extra were significantly ($P=0.05$) lower than NILs treated with RoundUp or the no-spray control.

Regardless of disease treatment or location, glyphosate treated RoundUp Ready® (glyphosate resistant) spring wheat, produced significantly ($P=0.001$) more grain than glyphosate sensitive NILs treated with Buctril/Harmony Extra or the no spray control.

This demonstrates green-bridge transmission of fungal pathogens, such as *Rhizoctonia* and Ggt, due to glyphosate application does not suppress yields of glyphosate resistant varieties; rather, glyphosate application increases yields demonstrating that the glyphosate treated plants not only resist the inoculated pathogens, but also other endemic pathogens, such as *Puccinia* spp. (rusts).

Example 6

This example describes the effect of herbicides on natural stripe rust infection of NILs of Bobwhite with and without glyphosate tolerance. The wheat was seeded and inoculated with *Rhizoctonia* and Ggt as described in Example 1. The yield results from the Pullman site are recorded in Table 6.

With reference to Table 6, the glyphosate treated glyphosate resistant wheat Bobwhite NILs produced superior yields regardless of what pathogen had been introduced. These results highlight the advantages of the disclosed method for conferring disease resistance on herbicide resistant wheat.

TABLE 6

Glyphosate induced yield enhancement of Bobwhite NILs in the presence of stripe rust in Pullman in 2002.

| Inoculation | Cultivar | Herbicide | Yield (bu/acre) |
|---|---|---|---|
| None | Bobwhite | None | 37.2 |
| None | Bobwhite (res.) | None | 36.8 |
| *Rhizoctonia* | Bobwhite | None | 38.7 |
| *Rhizoctonia* | Bobwhite (res.) | None | 33.9 |
| Ggt | Bobwhite | None | 37.7 |
| Ggt | Bobwhite (res.) | None | 32.8 |
| None | Bobwhite | Buctril/Harmony | 33.0 |
| None | Bobwhite (res.) | Buctril/Harmony | 31.8 |
| *Rhizoctonia* | Bobwhite | Buctril/Harmony | 39.4 |
| *Rhizoctonia* | Bobwhite (res.) | Buctril/Harmony | 36.3 |
| Ggt | Bobwhite | Buctril/Harmony | 37.7 |
| Ggt | Bobwhite (res.) | Buctril/Harmony | 26.4 |
| None | Bobwhite (res.) | Glyphosate | 44.9 |
| *Rhizoctonia* | Bobwhite (res.) | Glyphosate | 40.0 |
| GGT | Bobwhite (res.) | Glyphosate | 49.0 |

Example 7

This example describes the effect of glyphosate treatment of glyphosate resistant wheat in varying amounts and at different times. Eight different treatment regimens were applied to the hard white spring wheat variety Macon, which is susceptible to stripe rust. Macon plots were planted at the Palouse Conservation Farm near Pullman, Wash. and subjected to one of the following eight treatment regimens:

Treatment 1: no herbicide treatment and manual weed control;

Treatment 2: a 16 oz./A (0.50 kg/ha of active ingredient) application of glyphosate, one-half the recommended rate of 32 oz./A (1.0 kg/ha of active ingredient), was made 'on-label' to glyphosate resistant wheat at the 4-5 leaf stage.

Treatment 3: a first application of glyphosate at one-half (0.50 kg/ha of active ingredient) the recommended density of 1.0 kg/ha was made to glyphosate resistant wheat at the 4-5 leaf stage according to the manufacturer's instructions. A second application of 16 oz./A (0.50 kg/ha of active ingredient) glyphosate was made once moderate stripe rust symptoms appeared (42 days following the first glyphosate application).

Treatment 4: a 16 oz./A (0.50 kg/ha of active ingredient) application of glyphosate, one-half the recommended rate, was made to glyphosate resistant wheat once moderate stripe rust symptoms appeared.

Treatment 5: a 32 oz./A (1.0 kg/ha of active ingredient) application of glyphosate, the recommended full rate, was made 'on-label' to glyphosate resistant wheat at the 4-5 leaf stage.

Treatment 6: a first application of 32 oz./A. (1.0 kg/ha of active ingredient) glyphosate, the recommended full rate, was made 'on-label' to glyphosate resistant wheat at the 4-5 leaf stage and a second application of 32 oz./A. (1.0 kg/ha) glyphosate was made once moderate stripe rust symptoms appeared.

Treatment 7: a 32 oz./A. (1.0 kg/ha of active ingredient) application of glyphosate was made to glyphosate resistant wheat once moderate stripe rust symptoms appeared. Treatment 8: a 48 oz./A. (1.0 kg/ha of active ingredient) application of glyphosate, 1.5 times the recommended rate, was made to glyphosate resistant plants at the 4-5 leaf stage.

The results of the treatments listed above are recorded in Table 7.

TABLE 7

Yield of glyphosate-resistant wheat with variable timing of administration and amount of glyphosate.

| Treatment | Stripe Rust (96 days after planting) | Stripe Rust (102 days after planting) | Stripe Rust (106 days after planting) | Yield (bu/A) |
|---|---|---|---|---|
| No Spray | 9, 40% | 7-8, 70% | 8, 50% | 55.4 |
| No Spray | 9, 30% | 9, 50% | 8, 50% | 59.6 |
| 16 oz (52 days) | 7-8, 10% | 7-8, 30% | 8, 30% | 60.2 |
| 16 oz (52 days) and 16 oz (94 days) | 4-5, 10% | 0-1, 10% | 2, 10% | 68.7 |
| 16 oz (94 days) | 7-8, 20% | 2-3, 20% | 2-3, 15% | 52.7 |
| 32 oz (52 days) | 7-8, 20% | 7-8, 40% | 8, 60% | 80.3 |
| 32 oz (52 days) and 32 oz (94 days) | 9, 5% | 1-2, 5% | 3, 10% | 74.5 |
| 32 oz (94 days) | 7-8, 25% | 0-1, 20% | 2, 5% | 64.5 |
| 48 oz (52 days) | 7-8, 2% | 4-5, 10% | 8, 20% | 67.8 |

With reference to Table 7, stripe rust severity is characterized with two numerical indications. The first is a number characterizing the stripe rust severity on a scale of 0-9, with 0 corresponding to no infection and 9 being a high level of spore activity and infection. The second number is a percentage of the plants in the plot infected with the rating described by the first number.

With continued reference to Table 7, glyphosate resistant Macon experienced high levels of stripe rust infection when left untreated by glyphosate (rows 1 and 2). When glyphosate was applied to glyphosate resistant wheat at the 4-5 leaf stage, the 48 oz./A rate of glyphosate did the best job of controlling stripe rust compared to the 16 oz./A and 32 oz./A application. The higher rate of glyphosate clearly provided improved control of stripe rust infection.

When glyphosate was applied to glyphosate resistant Macon once plants had become moderately infected with stripe rust a curative effect was observed (rows 5 and 8). These "off-label" applications made 94 days after planting resulted in the formation of necrotic stripes on the leaves of the plants on the second day following glyphosate application. These necrotic stripes had been actively sporulating stripe rust at the time of glyphosate application. The amount of time needed to control stripe rust infection was found to be similar to when fungicides are applied to wheat plants infected with stripe rust.

The best control of stripe rust was seen for treatments 3 and treatments 6 (rows 4 and 7), which were treated with "split-treatments" of glyphosate. The stripe rust activity for both of these treatments 94 days after planting was similar to treatment 2 and treatment 4, before the second application of glyphosate was made. Once the second glyphosate application was made, a curative effect against active stripe rust was observed. These treatments had the lowest levels of stripe rust infection in the trial due to the initial fungicidal activity of glyphosate from the first (4-5 leaf stage; 52 days after planting) applications and the curative effects of glyphosate from the second applications. A curative effect was also noted when glyphosate was applied only once for treatments 4 and 7. These results demonstrate that the methods disclosed herein for treating glyphosate resistant wheat provide control of glyphosate sensitive weeds and control against the negative effects associated with fungal pathogens.

Example 8

This example describes the suppression of soybean rust using glyphosate treatment of glyphosate resistant soybean varieties.

Two different Roundup Ready soybean lines were used: Line 1 (purple flowers/grey pubescence) and Line 2 (white flowers/grey pubescence). Both lines are glyphosate resistant and have been classified as maturity group 3, with white or purple flowers and grey pubescence. The following treatments were used:

Treatment 1: No glyphosate spray before or after inoculation

Treatment 2: One application of glyphosate (48 oz./A) (1.0 kg/ha of active ingredient) three days before inoculation Treatment 3: Twice the amount of glyphosate as in Treatment 2 (96 oz./A) (2.0 kg/ha of active ingredient) applied three days before inoculation Treatment 4: One application of glyphosate (48 oz./A) three days before inoculation, and one application (48 oz./A) (1.5 kg/ha of active ingredient) when symptoms of soybean rust first appeared.

Treatment 5: No glyphosate spray before inoculation, and one application (48 oz./A) (1.5 kg/ha of active ingredient) when symptoms of soybean rust first appeared.

The results of this example are recorded in FIGS. 1-3. With reference to FIGS. 1-3, treatments 2 and 3 demonstrate that glyphosate treatment exerts a dose-dependent effect on soy rust. Treatments 4 and 5 demonstrate that glyphosate treatment of soybean infected with soy rust has a curative effect.

It will be apparent to those skilled in the art that various modifications and variations can be made in the disclosed methods without departing from the scope or spirit of the disclosure. Other embodiments of the methods will be apparent to those skilled in the art from consideration of the specification and practice of the procedures disclosed herein. It is intended that the specification and examples be considered as exemplary only, with a true scope and spirit of the invention being indicated by the following claims.

We claim:

1. A method for reducing disease on a wheat crop infected with at least one fungal pathogen selected from the group consisting of *Phakopsora* and *Puccinia*, comprising:

treating the wheat herbicide resistant crop infected with at least one fungal pathogen selected from the group consisting of *Phakopsora* and *Puccinia* with glyphosate in the absence of a fungicide to reduce effects of the at least one fungal pathogen selected from the group consisting of *Phakopsora* and *Puccinia* on the wheat herbicide resistant crop.

2. The method according to claim 1, wherein the step of treating comprises at least two separate applications of glyphosate.

3. The method according to claim 2, wherein more than two separate applications of glyphosate are applied to the wheat herbicide resistant crop at least seven days apart.

4. The method according to claim 1, wherein the treating step comprises treating the wheat herbicide resistant crop with 1.0 kg/ha to 3.0 kg/ha of glyphosate.

5. The method according to claim 1, wherein the treating step comprises treating the wheat herbicide resistant crop with about 1.0 kg/ha to 2.0 kg/ha of glyphosate.

6. The method according to claim 1, wherein treating step comprises treating the wheat herbicide resistant crop with 1.5 kg/ha to 2.0 kg/ha of glyphosate.

7. The method of claim 4, wherein the treating step comprises at least two separate applications of glyphosate.

8. The method of claim 1, wherein the pathogen is a foliar pathogen.

9. The method of claim 1, wherein the pathogen is *Phakopsora pachyrhizi.*

10. The method of claim 1, wherein the wheat herbicide resistant crop is glyphosate resistant wheat.

11. The method of claim 1, wherein the yield is 5% to about 20% higher than a crop not treated with glyphosate.

12. The method of claim 1, wherein the wheat herbicide resistant crop is glyphosate resistant wheat crop and the crop is treated with glyphosate at a stage between the 3 leaf stage and the flowering stage.

13. The method of claim 1, wherein the treating step comprises treating the wheat herbicide resistant crop with glyphosate prior to the display of a symptom of pathogen presence.

14. The method of claim 1, further comprising harvesting the crop thereby yielding a harvested crop.

15. A method for reducing disease on a glyphosate resistant wheat crop infected with at least one pathogen selected from the group consisting of *Phakopsora* and *Puccinia*, comprising:

treating the crop infected with the at least one pathogen selected from the group consisting of *Phakopsora* and *Puccinia* with glyphosate in the absence of a fungicide at a density of at least 1.0 kg/ha of glyphosate, thereby reducing the effects of the pathogen on the crop.

16. A method of using glyphosate to reduce adverse effects of fungal disease in a glyphosate resistant wheat crop, comprising the step of treating a glyphosate resistant wheat crop which has a fungal disease with glyphosate in the absence of a fungicide under conditions selected to be sufficient to inhibit growth or proliferation of fungal pathogens implicated in stripe rust in said glyphosate resistant wheat crop.

17. The method of claim 16 wherein said glyphosate is present in a herbicide composition.

18. The method of claim 16 wherein said fungal pathogens are selected from the group consisting of *Phakopsora* and *Puccinia*.

* * * * *